(12) United States Patent
DiCicco et al.

(10) Patent No.: US 12,588,947 B2
(45) Date of Patent: Mar. 31, 2026

(54) ELECTROSURGICAL DEVICE WITH AUTOMATIC SHUT-OFF

(71) Applicant: Boston Scientific Medical Device Limited, Galway (IE)

(72) Inventors: Matthew DiCicco, Toronto (CA); Gareth Davies, Toronto (CA); John Paul Urbanski, Toronto (CA); Eduardo Moriyama, Richmond (CA); Patrick Ryan, Toronto (CA); Daniel Wing Fai Mok, Mississauga (CA); Brandon Tyler, Mississauga (CA)

(73) Assignee: Boston Scientific Medical Device Limited, Galway (IE)

( * ) Notice: Subject to any disclaimer, the term of this patent is extended or adjusted under 35 U.S.C. 154(b) by 647 days.

(21) Appl. No.: 17/918,656

(22) PCT Filed: May 6, 2021

(86) PCT No.: PCT/IB2021/053876
§ 371 (c)(1),
(2) Date: Oct. 13, 2022

(87) PCT Pub. No.: WO2021/229383
PCT Pub. Date: Nov. 18, 2021

(65) Prior Publication Data
US 2023/0338082 A1 Oct. 26, 2023

Related U.S. Application Data

(60) Provisional application No. 63/022,842, filed on May 11, 2020.

(51) Int. Cl.
*A61B 18/14* (2006.01)
*A61B 18/00* (2006.01)

(52) U.S. Cl.
CPC ................... *A61B 18/1492* (2013.01); *A61B 2018/00083* (2013.01); *A61B 2018/00107* (2013.01);
(Continued)

(58) Field of Classification Search
CPC ...... A61B 18/1492; A61B 2018/00083; A61B 2018/00107; A61B 2018/00357; A61B 2018/00625
See application file for complete search history.

(56) References Cited

U.S. PATENT DOCUMENTS 175,254 A 3/1876 Oberly
827,626 A 7/1906 Gillet
(Continued)

FOREIGN PATENT DOCUMENTS

WO 2019/215618 A1 11/2019

OTHER PUBLICATIONS

International Search Report and Written Opinion received for PCT Patent Application No. PCT/IB2021/053876, mailed on Aug. 11, 2021, 11 pages.

*Primary Examiner* — Linda C Dvorak
*Assistant Examiner* — Abigail Bock
(74) *Attorney, Agent, or Firm* — Nelson Mullins Riley & Scarborough LLP

(57) ABSTRACT

A method and apparatus are disclosed for creating a puncture in a tissue. The assembly includes a puncturing device having a distal tip configured to deliver energy to the tissue, creating the puncture. The puncturing device further includes a marker positioned along the puncturing device. The assembly further includes a dilator which has a lumen extending from a proximal portion to a distal portion and configured to receive the puncturing device. The dilator further comprises a sensor positioned along a length of the
(Continued)

dilator. When the marker and the sensor are aligned, energy is delivered to the distal tip of the puncturing device.

9 Claims, 10 Drawing Sheets

(52) U.S. Cl.
CPC ............... *A61B 2018/00357* (2013.01); *A61B 2018/00625* (2013.01)

(56) References Cited

U.S. PATENT DOCUMENTS

| | | | |
|---|---|---|---|
| 848,711 A | 4/1907 | Weaver |
| 1,072,954 A | 9/1913 | Junn |
| 1,279,654 A | 9/1918 | Charlesworth |
| 1,918,094 A | 7/1933 | Geekas |
| 1,996,986 A | 4/1935 | Weinberg |
| 2,021,989 A | 11/1935 | Matthew |
| 2,146,636 A | 2/1939 | Lipchow |
| 3,429,574 A | 2/1969 | Williams |
| 3,448,739 A | 6/1969 | Stark et al. |
| 3,575,415 A | 4/1971 | Fulp et al. |
| 3,595,239 A | 7/1971 | Petersen |
| 4,129,129 A | 12/1978 | Amrine |
| 4,244,362 A | 1/1981 | Anderson |
| 4,401,124 A | 8/1983 | Guess et al. |
| 4,639,252 A | 1/1987 | Kelly et al. |
| 4,641,649 A | 2/1987 | Walinsky et al. |
| 4,669,467 A | 6/1987 | Willett et al. |
| 4,682,596 A | 7/1987 | Bales et al. |
| 4,790,311 A | 12/1988 | Ruiz |
| 4,790,809 A | 12/1988 | Kuntz |
| 4,793,350 A | 12/1988 | Mar et al. |
| 4,807,620 A | 2/1989 | Strul et al. |
| 4,832,048 A | 5/1989 | Cohen |
| 4,840,622 A | 6/1989 | Hardy |
| 4,863,441 A | 9/1989 | Lindsay et al. |
| 4,884,567 A | 12/1989 | Elliott et al. |
| 4,892,104 A | 1/1990 | Ito et al. |
| 4,896,671 A | 1/1990 | Cunningham et al. |
| 4,928,693 A | 5/1990 | Goodin et al. |
| 4,936,281 A | 6/1990 | Stasz |
| 4,960,410 A | 10/1990 | Pinchuk |
| 4,977,897 A | 12/1990 | Hurwitz |
| 4,998,933 A | 3/1991 | Eggers et al. |
| 5,006,119 A | 4/1991 | Acker et al. |
| 5,019,076 A | 5/1991 | Yamanashi et al. |
| 5,047,026 A | 9/1991 | Rydell |
| 5,081,997 A | 1/1992 | Bosley et al. |
| 5,098,431 A | 3/1992 | Rydell |
| 5,112,048 A | 5/1992 | Kienle |
| 5,154,724 A | 10/1992 | Andrews |
| 5,201,756 A | 4/1993 | Horzewski et al. |
| 5,209,741 A | 5/1993 | Spaeth |
| 5,211,183 A | 5/1993 | Wilson |
| 5,221,256 A | 6/1993 | Mahurkar |
| 5,230,349 A | 7/1993 | Langberg |
| 5,281,216 A | 1/1994 | Klicek |
| 5,300,068 A | 4/1994 | Rosar et al. |
| 5,300,069 A | 4/1994 | Hunsberger et al. |
| 5,314,418 A | 5/1994 | Takano et al. |
| 5,318,525 A | 6/1994 | West et al. |
| 5,327,905 A | 7/1994 | Avitall |
| 5,364,393 A | 11/1994 | Auth et al. |
| 5,372,596 A | 12/1994 | Klicek et al. |
| 5,380,304 A | 1/1995 | Parker |
| 5,397,304 A | 3/1995 | Truckai |
| 5,403,338 A | 4/1995 | Milo |
| 5,423,809 A | 6/1995 | Klicek |
| 5,425,382 A | 6/1995 | Golden et al. |
| 5,490,859 A | 2/1996 | Mische et al. |
| 5,497,774 A | 3/1996 | Swartz et al. |
| 5,507,751 A | 4/1996 | Goode et al. |
| 5,509,411 A | 4/1996 | Littmann et al. |
| 5,540,681 A | 7/1996 | Strul et al. |
| 5,545,200 A | 8/1996 | West et al. |
| 5,555,618 A | 9/1996 | Winkler |
| 5,571,088 A | 11/1996 | Lennox et al. |
| 5,575,766 A | 11/1996 | Swartz et al. |
| 5,575,772 A | 11/1996 | Lennox |
| 5,599,347 A | 2/1997 | Hart et al. |
| 5,605,162 A | 2/1997 | Mirzaee et al. |
| 5,617,878 A | 4/1997 | Taheri |
| 5,622,169 A | 4/1997 | Golden et al. |
| 5,624,430 A | 4/1997 | Eton et al. |
| 5,667,488 A | 9/1997 | Lundquist et al. |
| 5,673,695 A | 10/1997 | McGee et al. |
| 5,674,208 A | 10/1997 | Berg et al. |
| 5,683,366 A | 11/1997 | Eggers et al. |
| 5,720,744 A | 2/1998 | Eggleston et al. |
| 5,741,249 A | 4/1998 | Moss et al. |
| 5,766,135 A | 6/1998 | Terwilliger |
| 5,779,688 A | 7/1998 | Imran et al. |
| 5,810,764 A | 9/1998 | Eggers et al. |
| 5,814,028 A | 9/1998 | Swartz et al. |
| 5,830,214 A | 11/1998 | Flom et al. |
| 5,836,875 A | 11/1998 | Webster, Jr. |
| 5,849,011 A | 12/1998 | Jones et al. |
| 5,851,210 A | 12/1998 | Torossian |
| 5,885,227 A | 3/1999 | Finlayson |
| 5,888,201 A | 3/1999 | Stinson et al. |
| 5,893,848 A | 4/1999 | Negus et al. |
| 5,893,885 A | 4/1999 | Webster, Jr. |
| 5,904,679 A | 5/1999 | Clayman |
| 5,916,210 A | 6/1999 | Winston |
| 5,921,957 A | 7/1999 | Killion et al. |
| 5,931,818 A | 8/1999 | Werp et al. |
| 5,944,023 A | 8/1999 | Johnson et al. |
| 5,951,482 A | 9/1999 | Winston et al. |
| 5,957,842 A | 9/1999 | Littmann et al. |
| 5,964,757 A | 10/1999 | Ponzi |
| 5,967,976 A | 10/1999 | Larsen et al. |
| 5,989,276 A | 11/1999 | Houser et al. |
| 6,007,555 A | 12/1999 | Devine |
| 6,009,877 A | 1/2000 | Edwards |
| 6,013,072 A | 1/2000 | Winston et al. |
| 6,017,340 A | 1/2000 | Cassidy et al. |
| 6,018,676 A | 1/2000 | Davis et al. |
| 6,030,380 A | 2/2000 | Auth et al. |
| 6,032,674 A | 3/2000 | Eggers et al. |
| 6,048,349 A | 4/2000 | Winston et al. |
| 6,053,870 A | 4/2000 | Fulton, III |
| 6,053,904 A | 4/2000 | Scribner et al. |
| 6,056,747 A | 5/2000 | Saadat et al. |
| 6,063,093 A | 5/2000 | Winston et al. |
| 6,093,185 A | 7/2000 | Ellis et al. |
| 6,106,515 A | 8/2000 | Winston et al. |
| 6,106,520 A | 8/2000 | Laufer et al. |
| 6,117,131 A | 9/2000 | Taylor |
| 6,142,992 A | 11/2000 | Cheng et al. |
| 6,146,380 A | 11/2000 | Racz et al. |
| 6,155,264 A | 12/2000 | Ressemann et al. |
| 6,156,031 A | 12/2000 | Aita et al. |
| 6,171,305 B1 | 1/2001 | Sherman |
| 6,179,824 B1 | 1/2001 | Eggers et al. |
| 6,193,676 B1 | 2/2001 | Winston et al. |
| 6,193,715 B1 | 2/2001 | Wrublewski et al. |
| 6,210,408 B1 | 4/2001 | Chandrasekaran et al. |
| 6,217,575 B1 | 4/2001 | Devore et al. |
| 6,221,061 B1 | 4/2001 | Engelson et al. |
| 6,228,076 B1 | 5/2001 | Winston et al. |
| 6,245,054 B1 | 6/2001 | Fuimaono et al. |
| 6,267,758 B1 | 7/2001 | Daw et al. |
| 6,283,983 B1 | 9/2001 | Makower et al. |
| 6,292,678 B1 | 9/2001 | Hall et al. |
| 6,293,945 B1 | 9/2001 | Parins et al. |
| 6,296,615 B1 | 10/2001 | Brockway et al. |
| 6,296,636 B1 | 10/2001 | Cheng et al. |
| 6,302,898 B1 | 10/2001 | Edwards et al. |
| 6,304,769 B1 | 10/2001 | Arenson et al. |
| 6,315,777 B1 | 11/2001 | Comben |
| 6,328,699 B1 | 12/2001 | Eigler et al. |
| 6,360,128 B2 | 3/2002 | Kordis et al. |

(56) References Cited

U.S. PATENT DOCUMENTS

| | | |
|---|---|---|
| 6,364,877 B1 | 4/2002 | Goble et al. |
| 6,385,472 B1 | 5/2002 | Hall et al. |
| 6,394,976 B1 | 5/2002 | Winston et al. |
| 6,395,002 B1 | 5/2002 | Ellman et al. |
| 6,419,674 B1 | 7/2002 | Bowser et al. |
| 6,428,551 B1 | 8/2002 | Hall et al. |
| 6,450,989 B2 | 9/2002 | Dubrul et al. |
| 6,475,214 B1 | 11/2002 | Moaddeb |
| 6,485,485 B1 | 11/2002 | Winston et al. |
| 6,508,754 B1 | 1/2003 | Iprie et al. |
| 6,524,303 B1 | 2/2003 | Garibaldi |
| 6,530,923 B1 | 3/2003 | Dubrul et al. |
| 6,554,827 B2 | 4/2003 | Chandrasekaran et al. |
| 6,562,031 B2 | 5/2003 | Chandrasekaran et al. |
| 6,562,049 B1 | 5/2003 | Norlander et al. |
| 6,565,562 B1 | 5/2003 | Shah et al. |
| 6,607,529 B1 | 8/2003 | Jones et al. |
| 6,632,222 B1 | 10/2003 | Edwards et al. |
| 6,639,999 B1 | 10/2003 | Cookingham et al. |
| 6,650,923 B1 | 11/2003 | Lesh et al. |
| 6,651,672 B2 | 11/2003 | Roth |
| 6,662,034 B2 | 12/2003 | Segner et al. |
| 6,663,621 B1 | 12/2003 | Winston et al. |
| 6,702,811 B2 | 3/2004 | Stewart et al. |
| 6,709,444 B1 | 3/2004 | Makower |
| 6,723,052 B2 | 4/2004 | Mills |
| 6,733,511 B2 | 5/2004 | Hall et al. |
| 6,740,103 B2 | 5/2004 | Hall et al. |
| 6,752,800 B1 | 6/2004 | Winston et al. |
| 6,755,816 B2 | 6/2004 | Ritter et al. |
| 6,811,544 B2 | 11/2004 | Schaer |
| 6,814,733 B2 | 11/2004 | Schwartz et al. |
| 6,820,614 B2 | 11/2004 | Bonutti |
| 6,834,201 B2 | 12/2004 | Gillies et al. |
| 6,842,639 B1 | 1/2005 | Winston et al. |
| 6,852,109 B2 | 2/2005 | Winston et al. |
| 6,855,143 B2 | 2/2005 | Davison et al. |
| 6,860,856 B2 | 3/2005 | Ward et al. |
| 6,869,431 B2 | 3/2005 | Maguire et al. |
| 6,911,026 B1 | 6/2005 | Hall et al. |
| 6,951,554 B2 | 10/2005 | Johansen et al. |
| 6,951,555 B1 | 10/2005 | Suresh et al. |
| 6,955,675 B2 | 10/2005 | Jain |
| 6,970,732 B2 | 11/2005 | Winston et al. |
| 6,980,843 B2 | 12/2005 | Eng et al. |
| 7,029,470 B2 | 4/2006 | Francischelli et al. |
| 7,056,294 B2 | 6/2006 | Khairkhahan et al. |
| 7,083,566 B2 | 8/2006 | Tornes et al. |
| 7,112,197 B2 | 9/2006 | Hartley et al. |
| 7,335,197 B2 | 2/2008 | Sage et al. |
| 7,618,430 B2 | 11/2009 | Scheib |
| 7,651,492 B2 | 1/2010 | Wham |
| 7,666,203 B2 | 2/2010 | Chanduszko et al. |
| 7,678,081 B2 | 3/2010 | Whiting et al. |
| 7,682,360 B2 | 3/2010 | Guerra |
| 7,828,796 B2 | 11/2010 | Wong et al. |
| 7,900,928 B2 | 3/2011 | Held et al. |
| 8,192,425 B2 | 6/2012 | Mirza et al. |
| 8,257,323 B2 | 9/2012 | Joseph et al. |
| 8,388,549 B2 | 3/2013 | Paul et al. |
| 8,500,697 B2 | 8/2013 | Kurth et al. |
| 11,339,579 B1 | 5/2022 | Stearns |
| 2001/0012934 A1 | 8/2001 | Chandrasekaran et al. |
| 2001/0021867 A1 | 9/2001 | Kordis et al. |
| 2002/0019644 A1 | 2/2002 | Hastings et al. |
| 2002/0022781 A1 | 2/2002 | Mclntire et al. |
| 2002/0022836 A1 | 2/2002 | Goble et al. |
| 2002/0035361 A1 | 3/2002 | Houser et al. |
| 2002/0087153 A1 | 7/2002 | Roschak et al. |
| 2002/0087156 A1 | 7/2002 | Maguire et al. |
| 2002/0111618 A1 | 8/2002 | Stewart et al. |
| 2002/0123749 A1 | 9/2002 | Jain |
| 2002/0147485 A1 | 10/2002 | Mamo et al. |
| 2002/0169377 A1 | 11/2002 | Khairkhahan et al. |
| 2002/0188302 A1 | 12/2002 | Berg et al. |

| | | | |
|---|---|---|---|
| 2002/0198521 A1 | 12/2002 | Maguire | |
| 2003/0032929 A1 | 2/2003 | Mcguckin | |
| 2003/0040742 A1 | 2/2003 | Underwood et al. | |
| 2003/0144658 A1 | 7/2003 | Schwartz et al. | |
| 2003/0158480 A1 | 8/2003 | Tornes et al. | |
| 2003/0163153 A1 | 8/2003 | Scheib | |
| 2003/0225392 A1 | 12/2003 | Mcmichael et al. | |
| 2004/0015162 A1 | 1/2004 | Mcgaffigan | |
| 2004/0024396 A1 | 2/2004 | Eggers | |
| 2004/0030328 A1 | 2/2004 | Eggers et al. | |
| 2004/0044350 A1 | 3/2004 | Martin et al. | |
| 2004/0073243 A1 | 4/2004 | Sepetka et al. | |
| 2004/0077948 A1 | 4/2004 | Violante et al. | |
| 2004/0116851 A1 | 6/2004 | Johansen et al. | |
| 2004/0127963 A1 | 7/2004 | Uchida et al. | |
| 2004/0133113 A1 | 7/2004 | Krishnan | |
| 2004/0133130 A1 | 7/2004 | Ferry et al. | |
| 2004/0143256 A1 | 7/2004 | Bednarek | |
| 2004/0147950 A1 | 7/2004 | Mueller et al. | |
| 2004/0181213 A1 | 9/2004 | Gondo | |
| 2004/0230188 A1 | 11/2004 | Cioanta et al. | |
| 2005/0004585 A1 | 1/2005 | Hall et al. | |
| 2005/0010208 A1 | 1/2005 | Winston et al. | |
| 2005/0049628 A1 | 3/2005 | Schweikert et al. | |
| 2005/0059966 A1 | 3/2005 | Mcclurken et al. | |
| 2005/0065507 A1 | 3/2005 | Hartley et al. | |
| 2005/0085806 A1 | 4/2005 | Auge et al. | |
| 2005/0096529 A1 | 5/2005 | Cooper et al. | |
| 2005/0101984 A1 | 5/2005 | Chanduszko et al. | |
| 2005/0119556 A1 | 6/2005 | Gillies et al. | |
| 2005/0137527 A1 | 6/2005 | Kunin | |
| 2005/0149012 A1 | 7/2005 | Penny et al. | |
| 2005/0203504 A1 | 9/2005 | Wham et al. | |
| 2005/0203507 A1 | 9/2005 | Truckai et al. | |
| 2005/0261607 A1 | 11/2005 | Johansen et al. | |
| 2005/0288631 A1 | 12/2005 | Lewis et al. | |
| 2006/0041253 A1 | 2/2006 | Newton et al. | |
| 2006/0074398 A1 | 4/2006 | Whiting et al. | |
| 2006/0079769 A1 | 4/2006 | Whiting et al. | |
| 2006/0079787 A1 | 4/2006 | Whiting et al. | |
| 2006/0079884 A1 | 4/2006 | Manzo et al. | |
| 2006/0085054 A1 | 4/2006 | Zikorus et al. | |
| 2006/0089638 A1 | 4/2006 | Carmel et al. | |
| 2006/0106375 A1 | 5/2006 | Werneth et al. | |
| 2006/0135962 A1 | 6/2006 | Kick et al. | |
| 2006/0142756 A1 | 6/2006 | Davies et al. | |
| 2006/0189972 A1 | 8/2006 | Grossman | |
| 2006/0241586 A1 | 10/2006 | Wilk | |
| 2006/0247672 A1 | 11/2006 | Vidlund et al. | |
| 2006/0264927 A1 | 11/2006 | Ryan | |
| 2006/0276710 A1 | 12/2006 | Krishnan | |
| 2007/0060879 A1 | 3/2007 | Weitzner et al. | |
| 2007/0066975 A1 | 3/2007 | Wong et al. | |
| 2007/0118099 A1 | 5/2007 | Trout, III | |
| 2007/0123964 A1 | 5/2007 | Davies et al. | |
| 2007/0167775 A1 | 7/2007 | Kochavi et al. | |
| 2007/0208256 A1 | 9/2007 | Marilla | |
| 2007/0225681 A1 | 9/2007 | House | |
| 2007/0270791 A1 | 11/2007 | Wang et al. | |
| 2008/0039865 A1 | 2/2008 | Shaher et al. | |
| 2008/0042360 A1 | 2/2008 | Veikley | |
| 2008/0086120 A1 | 4/2008 | Mirza et al. | |
| 2008/0097213 A1 | 4/2008 | Carlson et al. | |
| 2008/0108987 A1 | 5/2008 | Bruszewski et al. | |
| 2008/0146918 A1 | 6/2008 | Magnin et al. | |
| 2008/0171934 A1* | 7/2008 | Greenan | A61B 5/06 |
| | | | 606/108 |
| 2008/0208121 A1 | 8/2008 | Youssef et al. | |
| 2008/0275439 A1 | 11/2008 | Francischelli et al. | |
| 2009/0105742 A1 | 4/2009 | Kurth et al. | |
| 2009/0138009 A1 | 5/2009 | Viswanathan et al. | |
| 2009/0163850 A1 | 6/2009 | Betts et al. | |
| 2009/0177114 A1 | 7/2009 | Chin et al. | |
| 2009/0182225 A1* | 7/2009 | Foley | A61B 18/24 |
| | | | 606/16 |
| 2009/0264977 A1 | 10/2009 | Bruszewski et al. | |
| 2010/0087789 A1 | 4/2010 | Leeflang et al. | |
| 2010/0125282 A1 | 5/2010 | Machek et al. | |
| 2010/0168684 A1 | 7/2010 | Ryan | |

(56)                    References Cited

U.S. PATENT DOCUMENTS

| | | | |
|---|---|---|---|
| 2010/0179632 A1 | 7/2010 | Bruszewski et al. | |
| 2010/0191142 A1 | 7/2010 | Paul et al. | |
| 2010/0194047 A1 | 8/2010 | Sauerwine | |
| 2011/0046619 A1 | 2/2011 | Ducharme | |
| 2011/0152716 A1 | 6/2011 | Chudzik et al. | |
| 2011/0160592 A1 | 6/2011 | Mitchell | |
| 2011/0190763 A1 | 8/2011 | Urban et al. | |
| 2012/0232546 A1 | 9/2012 | Mirza et al. | |
| 2012/0265055 A1 | 10/2012 | Melsheimer et al. | |
| 2012/0330156 A1 | 12/2012 | Brown et al. | |
| 2013/0184551 A1 | 7/2013 | Paganelli et al. | |
| 2013/0184735 A1 | 7/2013 | Fischell et al. | |
| 2013/0282084 A1 | 10/2013 | Mathur et al. | |
| 2014/0206987 A1 | 7/2014 | Urbanski et al. | |
| 2014/0276757 A1* | 9/2014 | Ellman | A61B 18/1402 |
| | | | 606/33 |
| 2014/0296769 A1 | 10/2014 | Hyde et al. | |
| 2015/0119639 A1 | 4/2015 | Ebata | |
| 2016/0058504 A1* | 3/2016 | Davies | A61B 8/4494 |
| | | | 600/424 |
| 2016/0220741 A1 | 8/2016 | Garrison et al. | |
| 2017/0172455 A1 | 6/2017 | Pressman et al. | |
| 2017/0325899 A1* | 11/2017 | Potter | A61B 5/062 |
| 2018/0070982 A1* | 3/2018 | Kimmel | A61B 18/1477 |
| 2019/0021763 A1 | 1/2019 | Zhou et al. | |
| 2019/0247035 A1 | 8/2019 | Gittard et al. | |
| 2020/0129049 A1 | 4/2020 | Panitz et al. | |

* cited by examiner

ELECTROSURGICAL DEVICE WITH AUTOMATIC SHUT-OFF

TECHNICAL FIELD

The disclosure relates to a surgical perforation device, configured to deliver energy to a tissue. More specifically, the invention relates to a device and method for creating a perforation in the atrial septum while using markers and sensors to control the delivery of energy.

BACKGROUND

Certain medical procedures require the use of a medical device that can create punctures or channels through tissues of the heart. Specifically, puncturing the septum of a heart creates a direct route to the left atrium where numerous cardiology procedures take place. One such device that gains access to the left atrium is a transseptal puncturing device which, in some devices, delivers radiofrequency energy from a generator into the tissue to create the perforation. The user positions the puncturing device at a target location on the fossa ovalis located on the septum of the heart and turns on the generator to begin delivering energy to the target location. The delivery of radiofrequency energy to a tissue results in vaporization of the intracellular fluid of the cells which are in contact with the energy delivery device. Ultimately, this results in a void, hole, or channel at the target tissue site.

Currently, the parameters around the delivery of energy involve the duration, as well as a pulsed or constant delivery of energy. Typically, the user will select the parameters, for example constant energy delivery for the duration of two seconds, prior to performing the puncture. The user activates the delivery via a push of a button on the generator or via a foot pedal. When the duration of energy delivery has been completed, the user will check, using various means (i.e., fluoroscopy, pressure readings, ultrasound, or contrast injections, etc.) to determine if the puncture was successful. If it was unsuccessful, the user will activate the energy delivery again. Once the duration is completed, the user will once again check to see if the puncture was successful. The user has the ability to turn off the delivery of energy before the duration is complete, using the button on the generator or the foot pedal, but there is still no way to confirm during the delivery of energy if the puncture was successful or not. This lack of knowledge around the success of the puncture during energy delivery may lead to inadvertent damage to surrounding tissues that are intended to be left unharmed during the procedure. For example, if the duration has been set for two seconds but the puncture has been completed in one second, the puncturing device is still delivering energy for additional time after entering the left atrium.

Inadvertent perforation of other tissues of the heart may result in general tissue damage within the left atrium, ancillary device damage (i.e., damage to pacemaker leads located in atrium) or potentially critical complications such as cardiac tamponade or inadvertent aortic perforation. A cardiac tamponade is a life-threatening complication of transseptal punctures which occurs when a perforation is created at the left atrial wall, left atrial roof, or left atrial appendage. This perforation of the atrial wall leads to an accumulation of fluid within the pericardial cavity around the heart. This buildup of fluid compresses the heart which in turn reduces the amount of blood able to enter the heart. An inadvertent aortic perforation is a rare life-threatening complication where the puncturing device enters and perforates the aorta which may require surgical repair.

Various minimally invasive procedures involve creating a puncture in a living tissue. One such procedure is performing a transseptal puncture which allows surgeons to gain access to the left side of the heart by creating a puncture from the right side of the heart through the septum. Recently, medical devices have been configured to perform the puncture by delivering energy, specifically radiofrequency energy, to the tissue. The delivery of radiofrequency energy to a tissue results in vaporization of the intracellular fluid of the cells which are in contact with the energy delivery device. This results in a perforation at the target tissue site. One of the complications which may arise during a transseptal puncture is the inadvertent puncturing of the left atrial wall or aorta. These potentially life-threatening complications may result in damage to surrounding tissue or ancillary devices, or perforation of the left atrial wall or aorta.

In light of these complications associated with inadvertent damage to surrounding tissues, there exists a need to provide a novel radiofrequency puncturing device wherein the delivery of radiofrequency energy is deactivated automatically after the puncture device has completed the puncture and entered the left atrium.

BRIEF DESCRIPTION OF THE DRAWINGS

In order that the invention may be readily understood, embodiments of the invention are illustrated by way of examples in the accompanying figures, in which.

DETAILED DESCRIPTION

Figure 1:
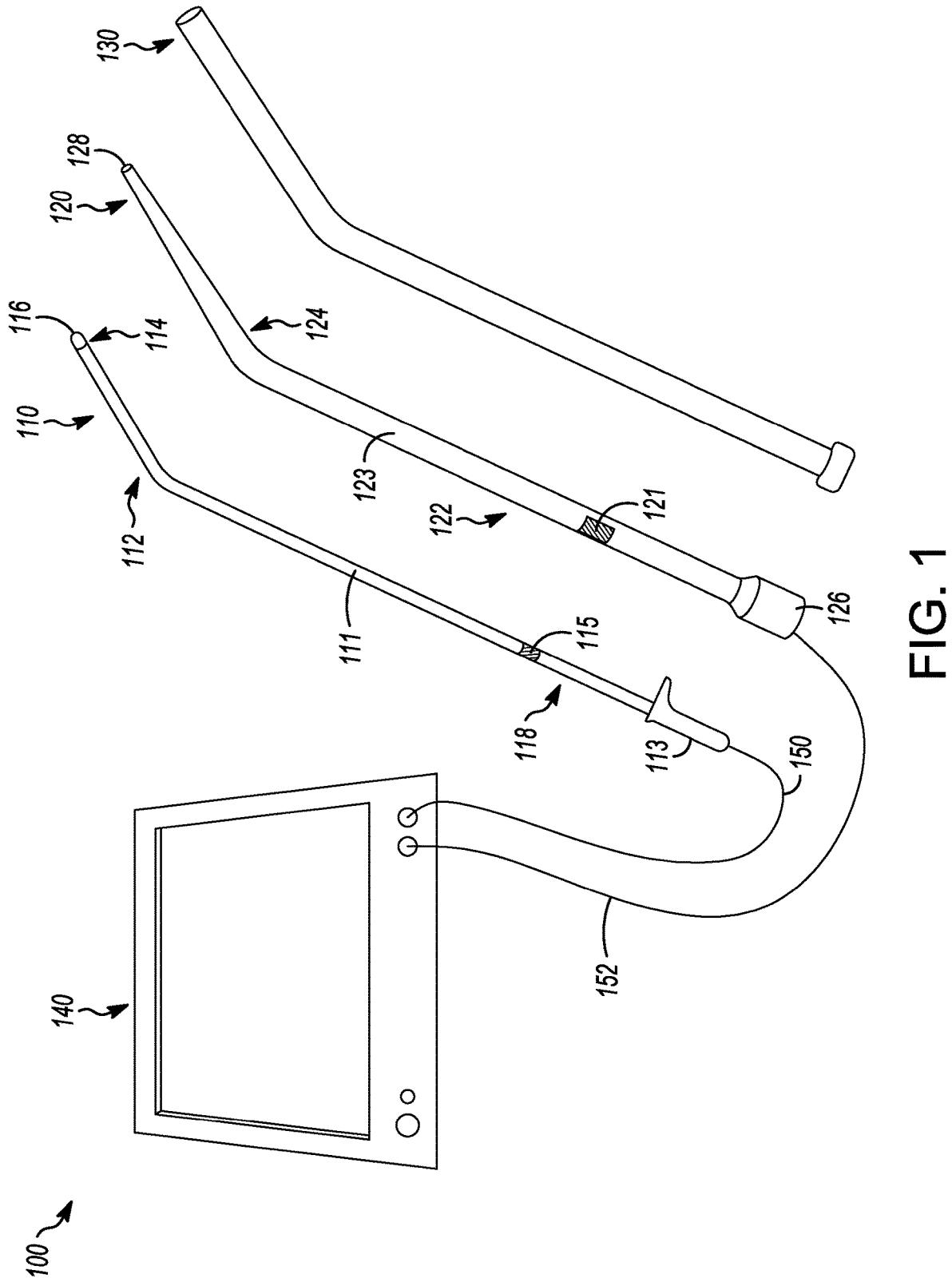
FIG. 1 is an illustration of an exemplary system which may be used to puncture tissue.

The problem of inadvertent puncturing of the left atrium is solved by providing an electrosurgical puncturing device with a mechanism to shut off the delivery of energy after the puncture of the septum has been completed.

In one broad aspect, embodiments of the present invention comprise an assembly to create a puncture in a tissue, comprising: a puncturing device comprising an elongate member having a distal tip configured to deliver energy to the tissue, creating the puncture. The puncturing device further comprises a marker positioned along the elongate member. A dilator wherein the dilator comprises a lumen extending from a proximal portion to a distal portion and configured to receive the puncturing device and further comprises a sensor positioned along a length of the dilator. When the marker and the sensor are aligned, energy is delivered to the distal tip of the puncturing device.

With specific reference now to the drawings in detail, it is stressed that the particulars shown are by way of example and for purposes of illustrative discussion of certain embodiments of the present device only. Before explaining at least one embodiment of the device in detail, it is to be understood that the device is not limited in its application to the details of construction and the arrangement of the components set forth in the following description or illustrated in the drawings. The device is capable of other embodiments or of being practiced or carried out in various ways. Also, it is to be understood that the phraseology and terminology employed herein is for the purpose of description and should not be regarded as limiting.

FIG. 1 illustrates an embodiment of a system 100 which may be used to gain access to the left atrium through a transseptal puncture. The system 100 comprises a puncturing device 110, a dilator 120, a sheath 130 and a generator 140. The puncturing device 110 comprises an elongate member 111 having a distal region 112 that ends in a distal tip 114. The distal tip 114 comprises an energy delivery device 116, such as an electrode, that is configured to deliver energy to a tissue. The puncturing device 110 further comprises a proximal portion 118 that ends in a hub 113 which is connected to the generator 140 via a connector cable 150. The generator 140 is capable of delivering energy to the puncturing device 110 which travels along the elongate member 111 from the hub 113 to the energy delivery device 116 at the distal tip 114. The puncturing device 110 is preferably constructed from a conductive material, such as stainless steel or nitinol. The puncturing device 110 may be comprised of a solid, core wire, or a hollow tube, and may end in an atraumatic distal tip 114. In order to ensure that the energy is delivered to the tissue by the energy delivery device 116, the puncturing device 110 may be coated in any type of insulating material, such as PTFE (polytetrafluoroethylene), leaving the energy delivery device 116 exposed at the distal tip 114. A marker 115 may be positioned anywhere along the length of the elongate member 111, in either the proximal 118 or distal portion 112. The marker 115 may be a colour band, bar code band, a band with a distinct surface roughness, or a band comprised of or doped with magnetic or conductive material.

The dilator 120 comprises an elongate member 123 with a proximal portion 122 and a distal portion 124. The proximal portion 122 of the dilator ends in a hub 126, while the distal portion 124 tapers down to an open distal tip 128. A lumen (not shown) extends within the elongate member 123 between the hub 126 and the distal tip 128. The lumen is sufficiently large enough such that the puncturing device 110 may be inserted into the hub 126 and move through the lumen. In use, the distal tip 114 of the puncturing device 110 extends past the distal tip 128 of the dilator 120. The dilator 120 may be comprised of a harder material, such as high-density polyethylene (HDPE) or a softer material, for example polyurethane or polyether block amide. Embedded into the elongate member 123 body, in the proximal 122 or distal 124 region is a detector 121 which is able to detect the marker 115 positioned along the length of the elongate member 111 of the puncturing device 110. The detector 121 may be a colour sensor, barcode reader, light intensity sensor, magnetic sensor, or a capacitance proximity sensor. The detector 121 can be hooked up to the generator 140 via a connector cable 152 that extends from the detector 121 and exits out of the hub 126 of the dilator 120.

In use, when the puncturing device 110 is inserted into the dilator 120, the alignment of the marker 115 and the detector 121 would send a signal to the generator 140 via the connector cable 152 of the dilator 120, which in turn would enable the delivery of energy from the generator 140 to the puncturing device 110 via the connector cable 150. If the marker 115 and detector 121 are not aligned, energy delivery is disabled.

An exemplary method involving the embodiment of the system 100 described above, involves the steps of delivering energy through the energy delivery device 116 to an atrial septum of a patient's heart, advancing the energy delivery device 116 through the puncture and automatically disabling the delivery of energy upon completion of puncture. The steps towards performing the transseptal puncture may include:

(i) gaining access to the vasculature through the groin to the femoral vein and advancing the assembly (i.e., puncturing device 110, dilator 120 and sheath 130) into the right atrium of the heart through the inferior vena cava. At this stage, the distal tip 114 of the puncturing device 110 is slightly protruding from the distal tip 128 of the dilator 120 and sheath 130. The marker 115 of the puncturing device 110 would be aligned with the detector 121 of the dilator 120 which enables the delivery of energy.

(ii) The distal tip 114 of the puncturing device 110 is maneuvered to the target location, for example, the fossa ovalis on the atrial septum. When in position, the user activates energy delivery on the generator 140 which will send energy to the energy delivery device 116. This energy may be in the high frequency range, such as radiofrequency energy.

(iii) Upon completion of the puncture, the puncturing device 110 is pushed through the puncture into the left atrium. At this point, the marker 115 of the puncturing device 110 and the detector 121 of the dilator 120 are no longer aligned, and the delivery of energy is disabled, automatically shutting off.

(iv) The dilator 120 and sheath 130 are then pushed through the puncture and access to the left atrium is achieved.

Figures 2A, 2B, 2C:
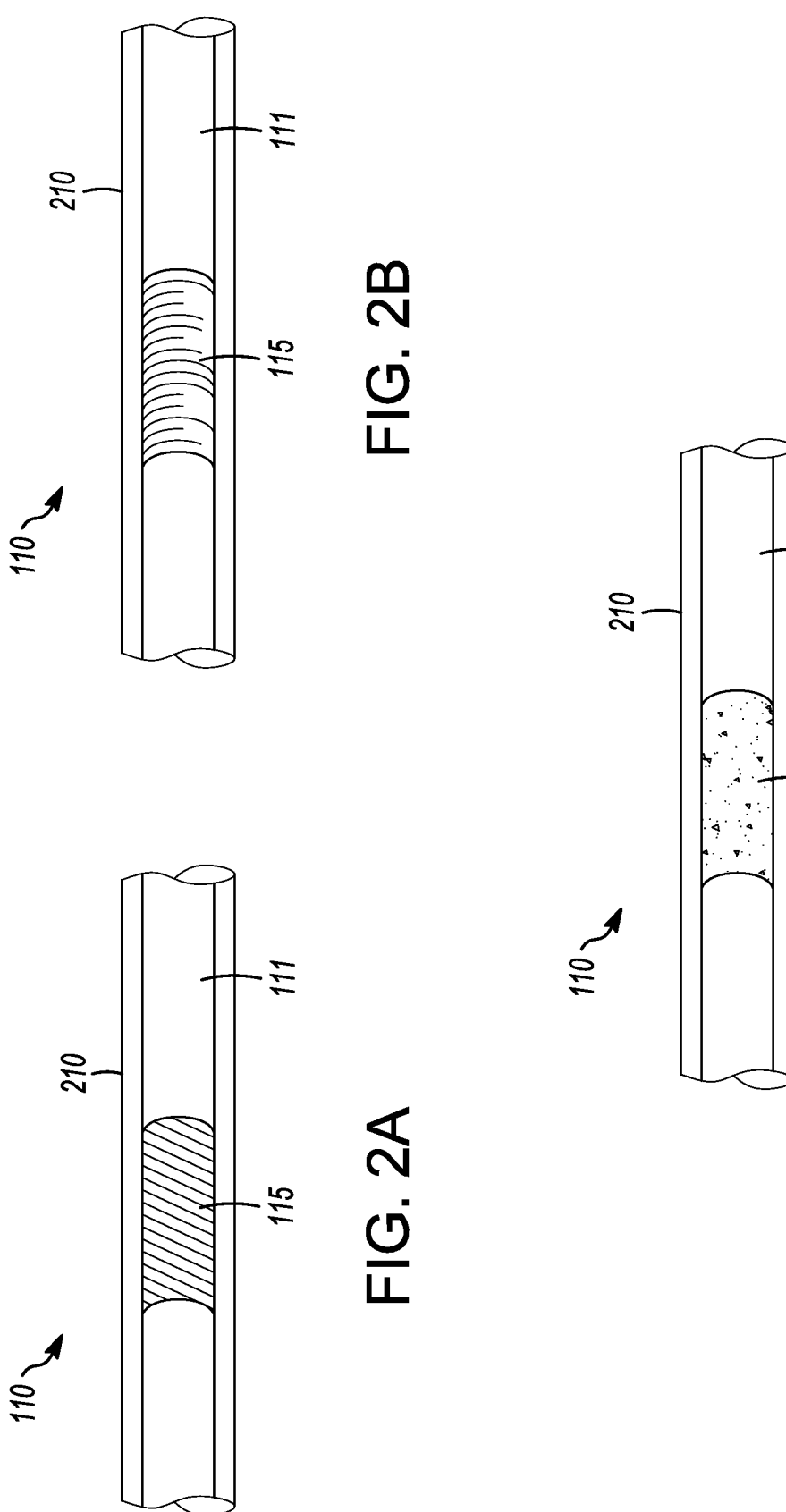
FIG. 2a-2e are illustrations of various marker bands which may be placed on the puncturing device.

As previously described above, the marker 115 located on the puncturing device 110 may be any type of detectable band. FIG. 2a illustrates an embodiment of the puncturing device 110 which has a marker 115 comprising a unique colour band. In this embodiment, the colour band may be applied as a spray coating directly to the elongate member 111 or as a heat shrink sleeve on top of the elongate member 111. A coating of clear electrically insulative material 210 (i.e., such as a clear coat of polytetrafluorethylene (PTFE)) may be applied on top of elongate member 111, either over just the colour band or the entire length of the elongate member 111, to ensure that the marker 115 can be optically detected by the colour sensor detector 121 located on the dilator.

In an alternative embodiment, the marker 115 comprises a unique barcode or Radio Frequency Identification (RFID) code, as illustrated in FIG. 2b. This may be applied as a heat shrinkable sleeve with a unique barcode on it or a heat shrinkable sleeve of a solid colour may be applied and using a laser, different lines may be ablated into the sleeve. For example, if a blue sleeve was applied to the elongate member 111, the laser ablation would create white lines onto the sleeve. A clear coat of electrically insulating material 210 may be applied over the elongate member 111 where the marker 115 is located or over its entire length. This would ensure that the barcode is optically detected by the barcode reader on the dilator.

In some embodiments, the marker 115 comprises a band with a different surface roughness than the elongate member 111. During manufacturing, the change in surface roughness may be directly applied to the elongate member 111 during the manufacturing process, as seen in FIG. 2*c*. Alternatively, the marker 115 may be a band with different surface roughness may be placed over top of the elongate member 111. The band may be swaged over the elongate member 111 or may be fit over top, either in tight or loose fit.

Similarly, to the previous embodiments, a clear layer of electrically insulative material 210 may be applied over the elongate member 111, over the marker 115 or the entire length of the member 111, to allow for the detection of light intensity by the sensor in the dilator.

Figure 2D:
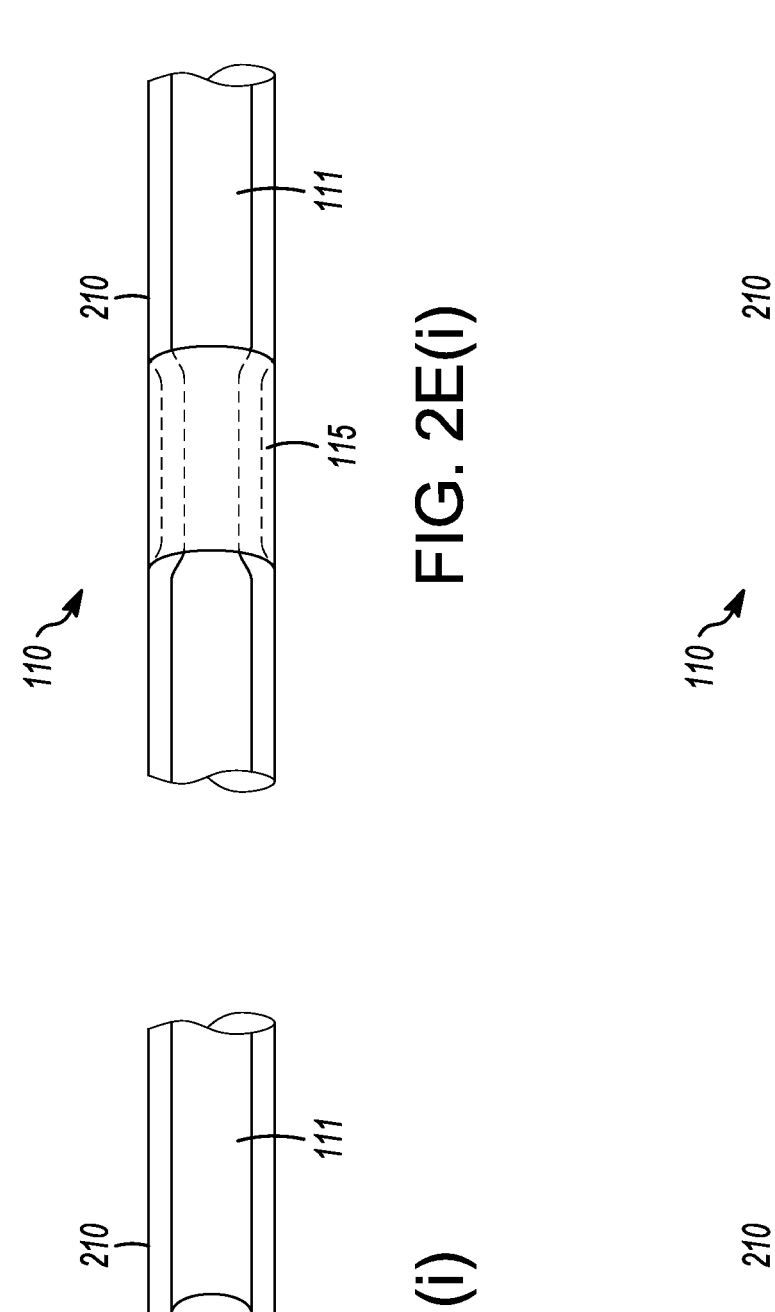

In another embodiment, the marker 115 on the puncturing device 110 is comprised of a magnetic material. The band may be comprised of a magnetic material, for example a band of any magnetic metal, or may be comprised of a non-metal band that is doped with magnetic material, such as metal doped plastic. For both the magnetic metal band or doped plastic, the marker 115 may be a mechanical fit that is swaged over the elongate member 111, as illustrated in FIG. 2*d*(*i*), or the band may be fitted over the elongate member 111, in a tight or loose fit around the shaft, as illustrated in FIG. 2*d*(*ii*). The elongate member 111 may have an electrically insulating layer 210 which covers its entire length and may act to confine the band in place. Alternatively, in embodiments that use a doped plastic band as a marker 115, this may be applied as a heat shrinkable plastic tube doped with magnetic material which can be applied over top of the elongate member 111.

Figure 2E:
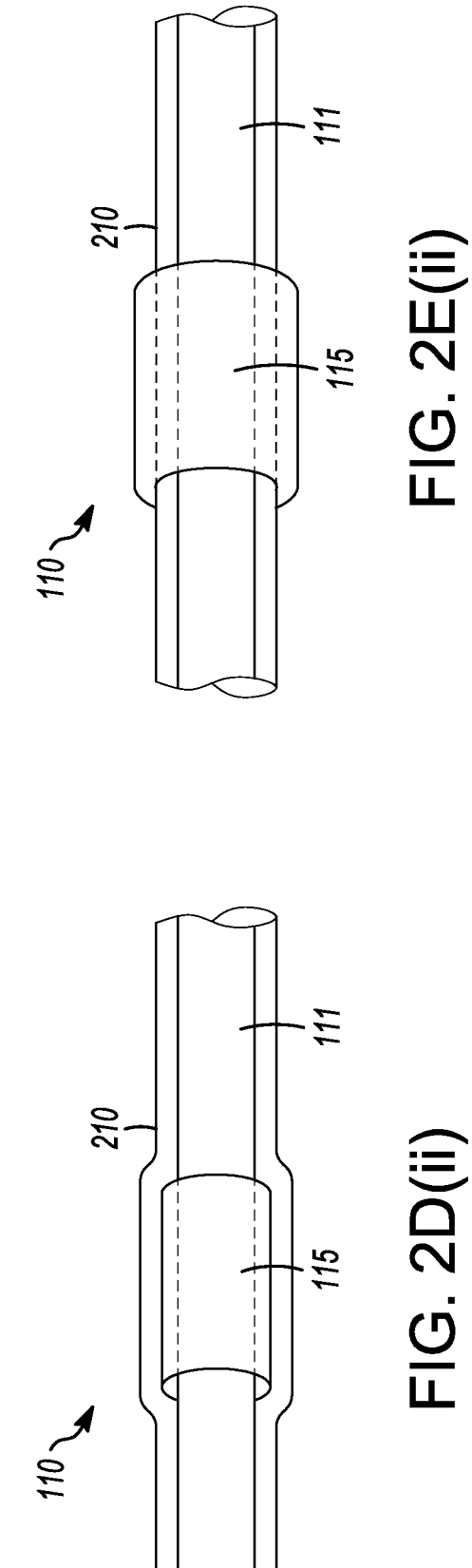

In an alternative embodiment, the marker 115 on the puncturing device 110 is comprised of a conductive material. The marker 115 may be a band comprised fully of a conductive material or a non-metal material that has been doped with conductive material (i.e., a doped plastic band). In these embodiments, the band will need to be placed over top of the insulating layer 210 in order to ensure that it communicates with the detector in the dilator and does not interfere with the delivery of energy along the elongate member 111. For both the conductive metal band or doped plastic band, the marker 115 may be a mechanical fit that is swaged over top the insulating layer 210, as illustrated in FIG. 2*e*(*i*), or the band may be fitted over the insulating layer 210 in a tight fit to ensure that the band does not shift, as illustrated in FIG. 2*e*(*ii*). In an alternate embodiment, the marker 115 may be comprised of a heat shrinkable plastic tube that has been doped with conductive material which can be applied over top of the insulating material 210.

In any of the previously described embodiments, the marker 115 may be placed anywhere along the proximal or distal portion of the puncturing device 110 as long as the placement of the marker 115 aligns with the detector 121 in the dilator in a position which would allow the delivery of energy when the puncturing device 110 is in the correct position within the dilator.

Figures 3A, 3B:
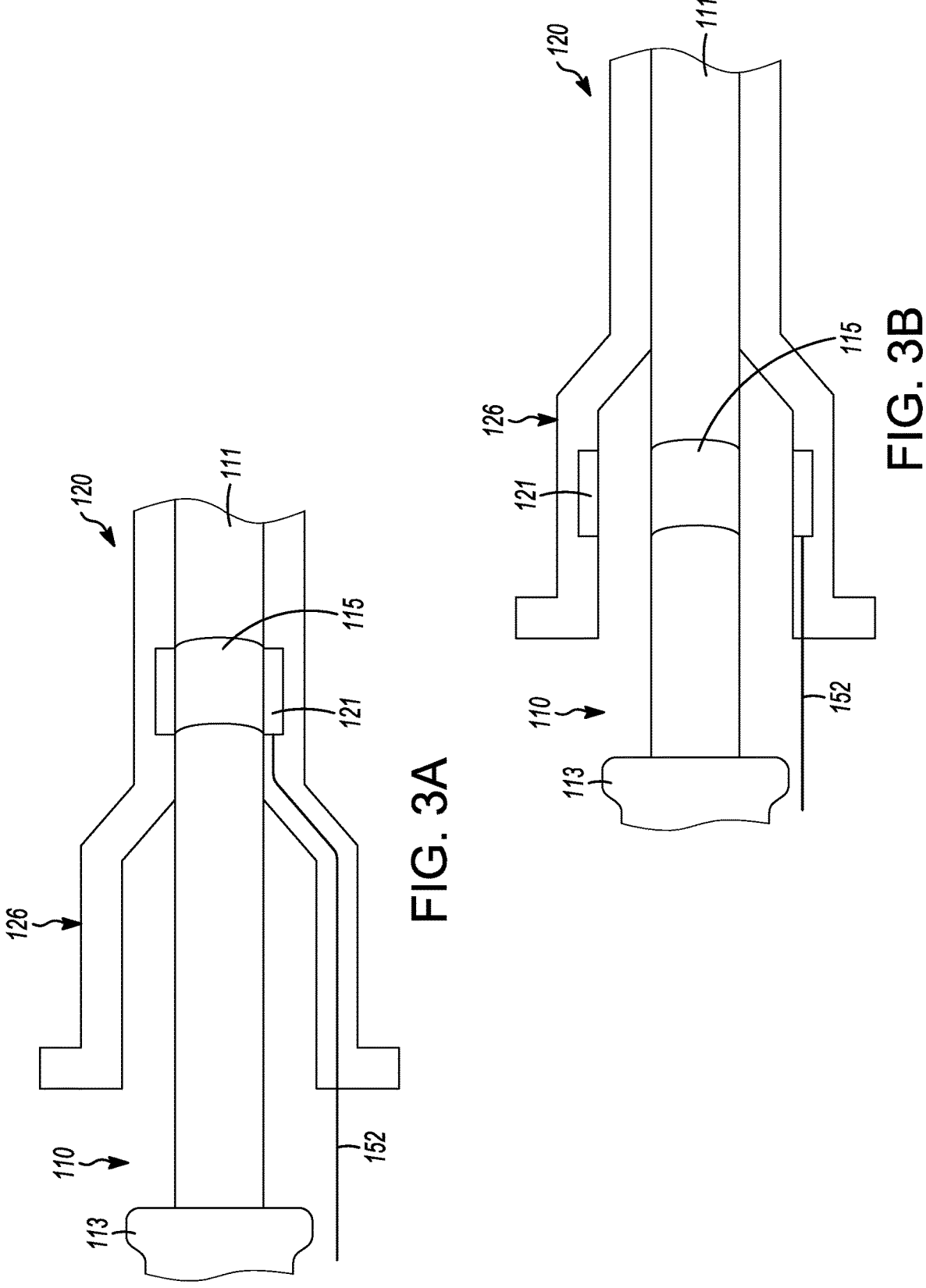
FIG. 3a-3b are illustrations of various detector placements on the dilator.

With reference to FIG. 3*a*, the dilator 120 comprises a detector 121 which will be able to detect the marker 115 located on the puncturing device 110. This detection may be used to enable and disable the delivery of energy from the generator to the distal tip of the puncturing device 110. For example, when the marker 115 and the detector 121 are aligned, energy delivery is enabled; if the marker 115 and the detector 121 are not aligned, energy deliver is disabled. The position of the detector 121 may be anywhere along the dilator 120. In one embodiment, the detector 121 is positioned on the elongate member 123 of the dilator 120, in the proximal portion, as seen in FIG. 3*a* or it may be positioned in the distal portion (not shown). This embodiment may be ideal as it allows for a tight fit between the detector 121 and marker 115 without the potential interference of blood or fluid. Alternatively, the detector 121 is positioned in the hub 126 of the dilator 120, as illustrated in FIG. 3*b*. The detector 121 is embedded into the wall of the dilator 120 and may comprise a colour sensor, barcode reader, light intensity sensor, magnetic sensor, or spring contacts that close connections in the presence of the conductive ring, for example.

In some embodiments, the detector 121 may be a colour sensor which would be able to detect the marker 115 band which is a unique colour. For example, the sensor would shine a white light onto the elongate member 111 and would then record the reflected light.

The sensor may comprise a red, green, and blue colour filter which would be able to convert the amount of light to current. Additionally, the sensor may also comprise a converter to then convert the current into a voltage that may be sent to the generator. From there, the generator may have a switch, either implemented as hardware (such as a voltage-based switch) or software (such as a computer algorithm). This may then be used to enable or disable the delivery of energy to the puncturing device 110.

In an alternative embodiment, the detector 121 may be a barcode reader or a barcode scanner which would be able to read the barcode information on the marker 115 of the puncturing device 110 and send the information to the generator. The scanner may shine a laser onto the barcode on the marker 115 which is reflected off the barcode into a photoelectric cell; light sections will reflect more light than the dark sections. The photoelectric cell may then generate a pattern of "on" or "off" pulses (i.e., "on" would be a light section, "off" would be a dark section). The barcode reader or scanner would then convert this information into a binary code which can be sent back to the generator. This may be used to enable or disable the delivery of energy to the puncturing device 110.

In some embodiments, the detector 121 may be a light intensity sensor to detect the amount of light reflected from a surface. In this embodiment, the detector 121 would determine the amount of light reflected from the elongate member 111, as well as the amount of light reflected from a marker 115 with a rough surface. For example, the detector 121 may be a photoelectric sensor comprising a light source and a receiving element. The light source may direct a beam of light onto the elongate member 111 which will be reflected back to the receiving element and converts it to either an analog (i.e., voltage) or digital (i.e., "on" or "off") output based on the amount of light reflected back. This output may then communicate with the generator to enable or disable energy delivery to the puncturing device 110. This may be implemented as a hardware switch or a software algorithm.

In another embodiment, the marker 115 on the puncturing device 110 may comprise a magnetic band and while the detector 121, to detect magnetic fields, would be placed in the dilator 120. This type of sensor would detect the magnetic field present in the magnetic band of the device 110. Generally, if there is a magnetic field, the sensor may output a binary signal which may be used to control the delivery of energy to the puncturing device 110. For example, if a magnetic field is present (i.e., the marker 115 is aligned with the detector 121) the sensor may output an "on" signal. In contrast, if no magnetic field is present, the sensor may output an "off" signal. These signals may be communicated back to the generator to control the delivery of energy.

In some embodiments, the marker 115 may comprise a metal band. The detector 121 in the dilator 120 may be in the form of a capacitance proximity sensor. This type of sensor world work similar to the magnetic sensor, detecting a metal (magnetic or non-magnetic) band along the puncture device 110. When the marker 121 is not aligned with the detector 121, the detector 121 will not sense the band. This would signal the generator to disable the delivery of energy to the puncturing device 110. However, when the marker 115 is positioned such that it is detected by the capacitance proximity sensor, it will elicit a response from the generator to enable the delivery of energy to the puncturing device 110. This may be implemented as a software algorithm, for example if there the marker 115 is detected, enable energy delivery; if not, disable energy delivery.

For the detector 121 to communicate with the generator, an insulative connector cable 152 will need to run from the detector 121 to the generator. This will signal the generator to enable the delivery of energy when the marker 115 and detector 121 are aligned or disable the delivery of energy when they are not aligned.

Figure 3C:
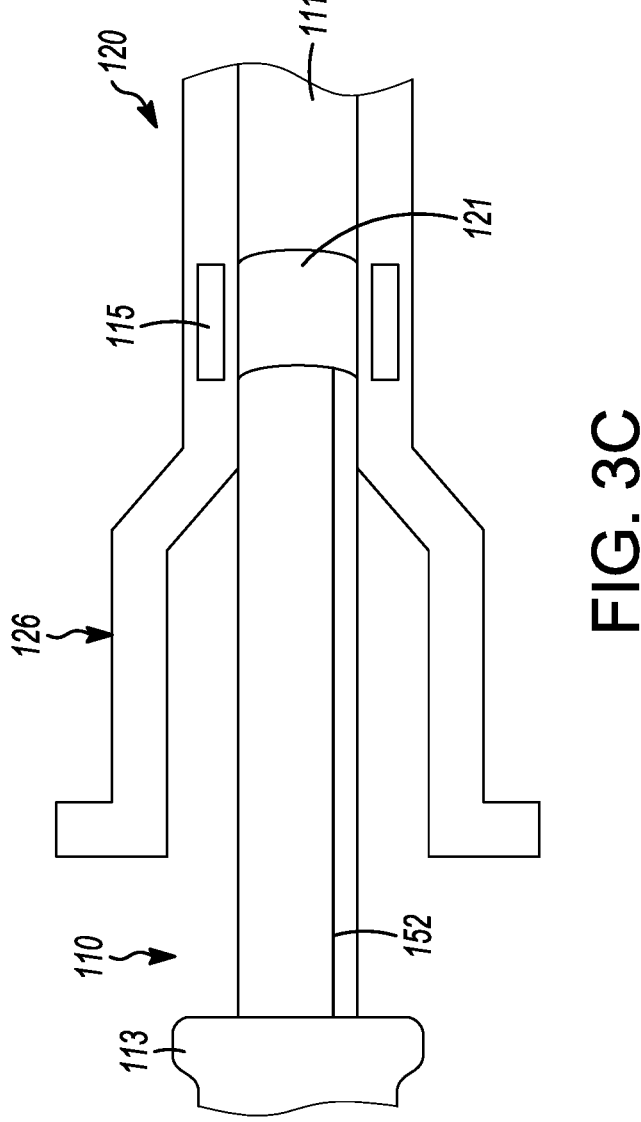
FIG. 3c is an illustration of the detector being placed on the puncturing device with a marker being placed on the dilator.

In an alternative embodiment, the puncturing device 110 comprises the detector 121 while the dilator 120 comprises the marker 115. An example of this embodiment is illustrated in FIG. 3*c*. Similarly, to the previously described embodiments, the marker 115 may comprise a colour band, bar code band, a band with a distinct surface roughness, or a band comprised of or doped with magnetic or conductive material, for example. These bands may be embedded into the dilator 121. The detector 121 may be any sensor with the ability to detect the maker 115, such as a colour sensor, barcode reader, light intensity sensor, magnetic sensor, or a capacitance proximity sensor. For some markers 115, the material of the dilator may need to be comprised of a transparent material such that the optical detectors 121 would be able to detect when the marker 115 has been aligned. For example, the colour band and colour sensor, the barcode marker and barcode reader, as well as the marker with a surface roughness and light intensity sensor, use light transmission and receiving to detect and thus would need a transparent material. The marker 115 and detector 121 may be located anywhere along the length of the dilator 120 or puncturing device 110 (i.e., proximal or distal portions), if they are index to the proper locations for the automatic shut-off to function. For these embodiments, the connector cable 152 is insulated and runs along the length of the elongate member 111, exiting out of the hub 113 of the puncturing device 110. The connector cable 152 may be contained with the cable used to deliver energy to the puncturing device 110 so that the user would only need to plug in one cable to the generator rather than the two cables (i.e., one from the puncturing device 110 and one from the dilator 120) of the previously described embodiments.

Figure 4A:
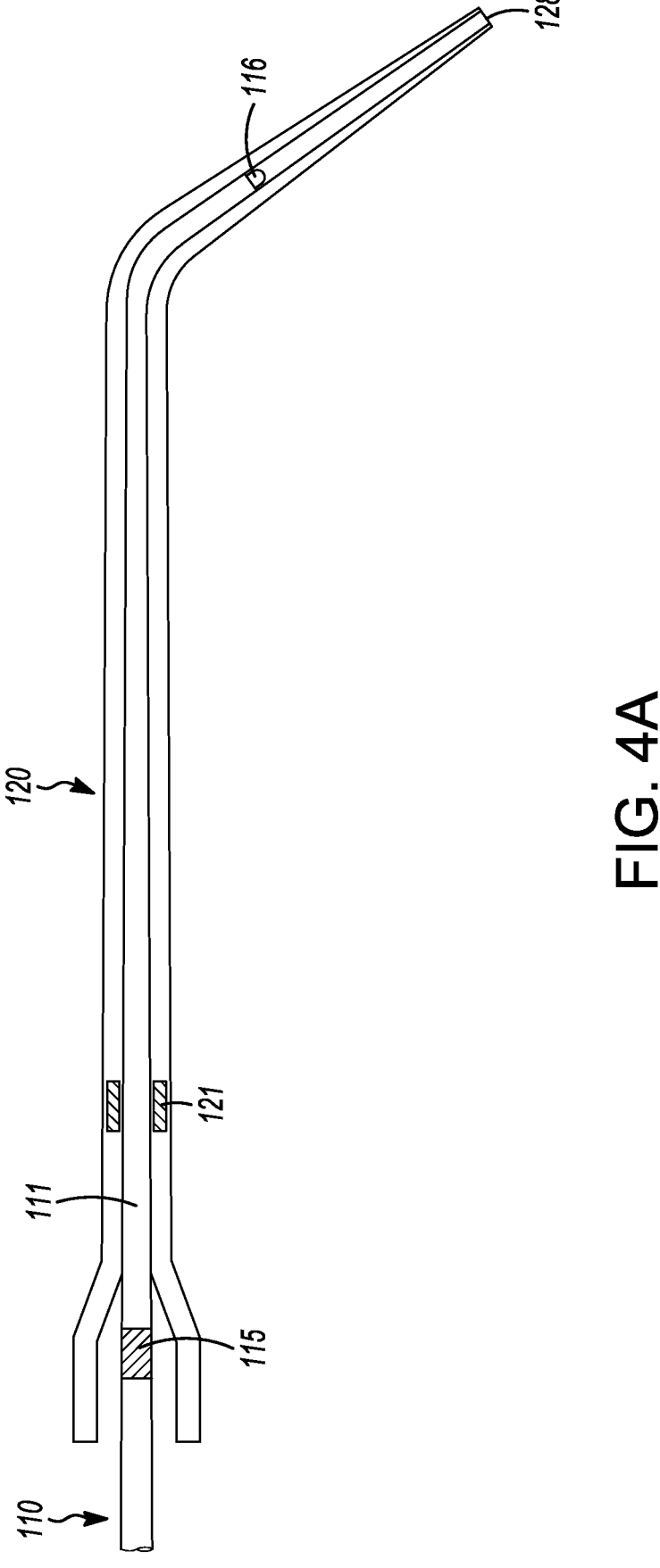
FIG. 4a-4c are illustrations of the puncturing device moving through the dilator, illustrating the alignment of the marker and detector.
Figure 4B:
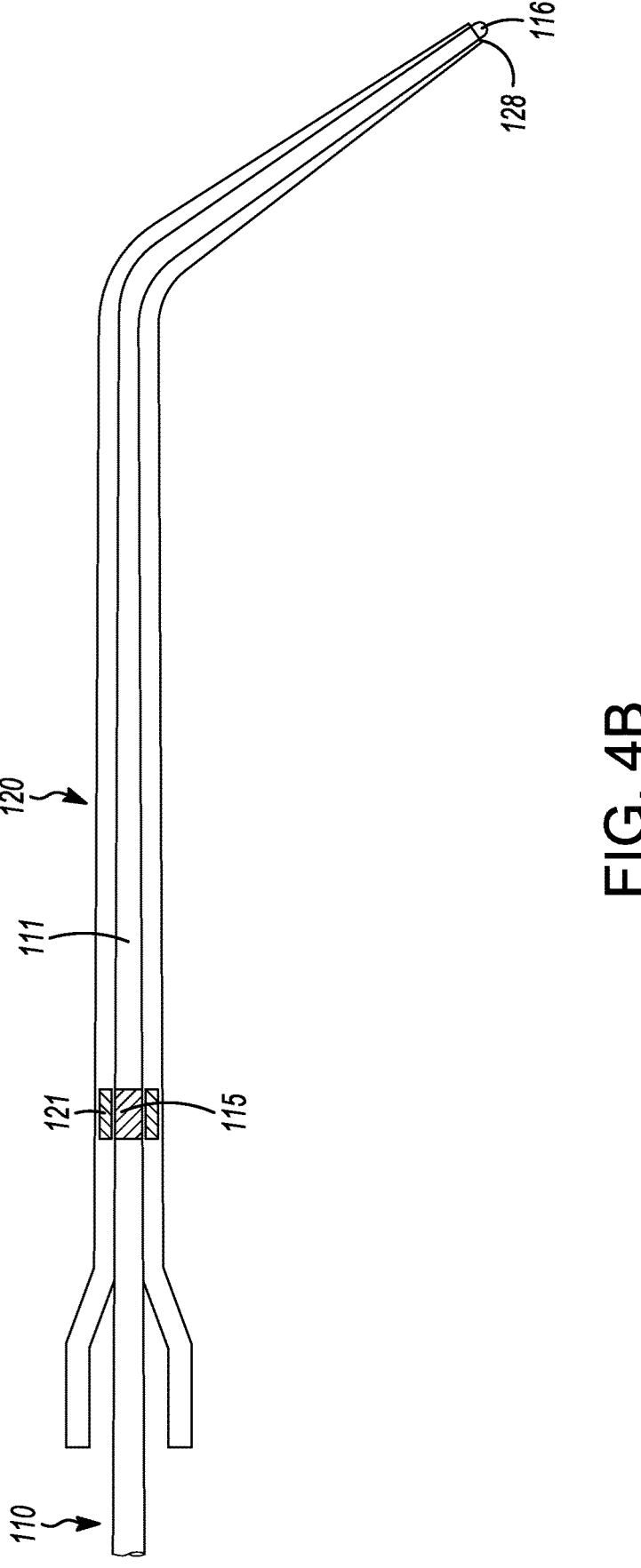
Figure 4C:
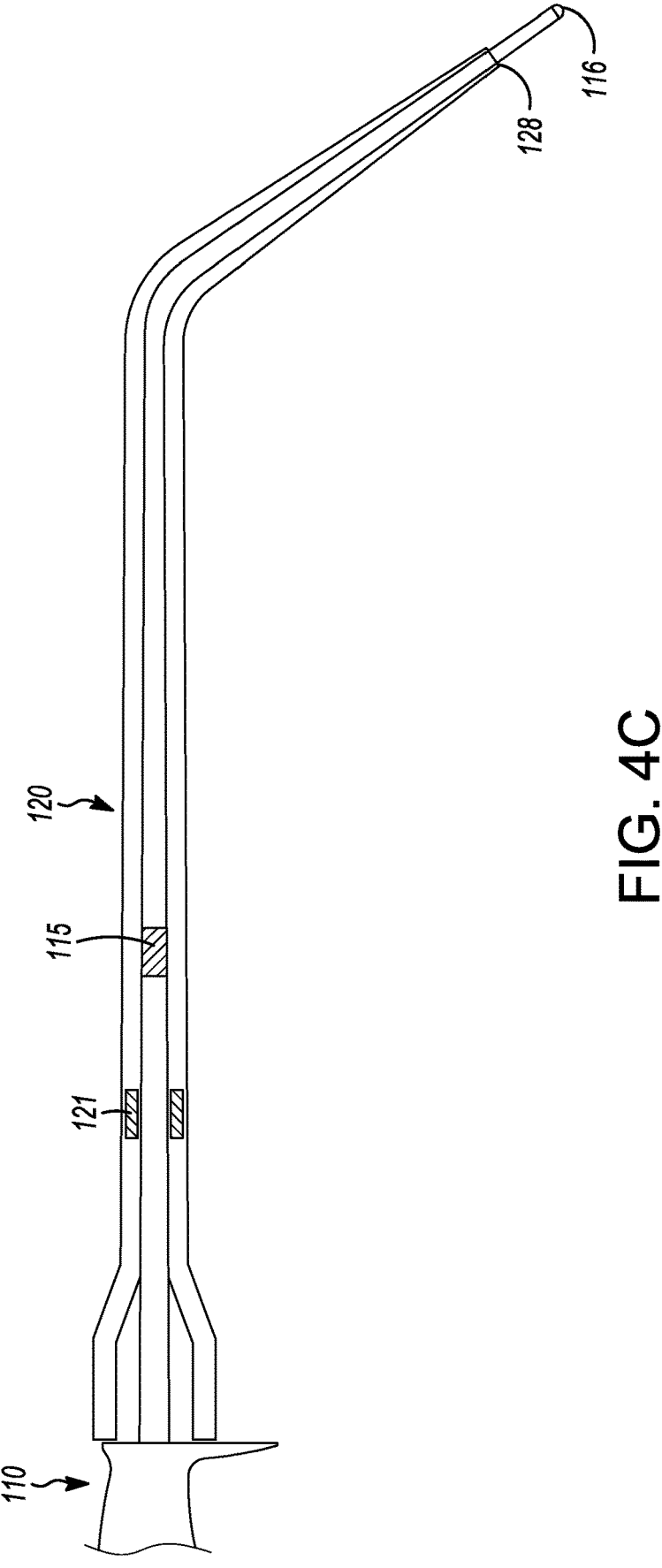

FIG. 4*a*-4*c* illustrate the puncturing device 110, comprising a marker 115, and the dilator 120, comprising a detector 121, as the puncturing device 110 moves along the length of the dilator 120. FIG. 4*a* illustrates the puncturing device 110 in a position where the energy delivery device 116 is still contained within the dilator 120, prior to puncture. At this stage, the marker 115 and detector 121 are not aligned, and therefore energy is not able to be delivered to the energy delivery device 116. Energy delivery is enabled when the marker 115 and detector 121 are aligned, this would occur when the energy delivery device 116 is slightly protruding from distal tip 128 of the dilator 121 (FIG. 4*b*). When energy delivery is enabled, this may be signalled to the user via a sound or prompt on the generator. The user will then activate energy delivery to create a puncture in the tissue. Once the puncture is complete, the puncturing device 110 moves through the puncture, such that the energy delivery device 116 moves past the distal tip 128 of the dilator 121. In turn, the marker 115 and the detector 121 are no longer aligned (FIG. 4*c*). As a result, energy delivery to the puncturing device 110 will be disabled, automatically shutting off.

Figure 5A:
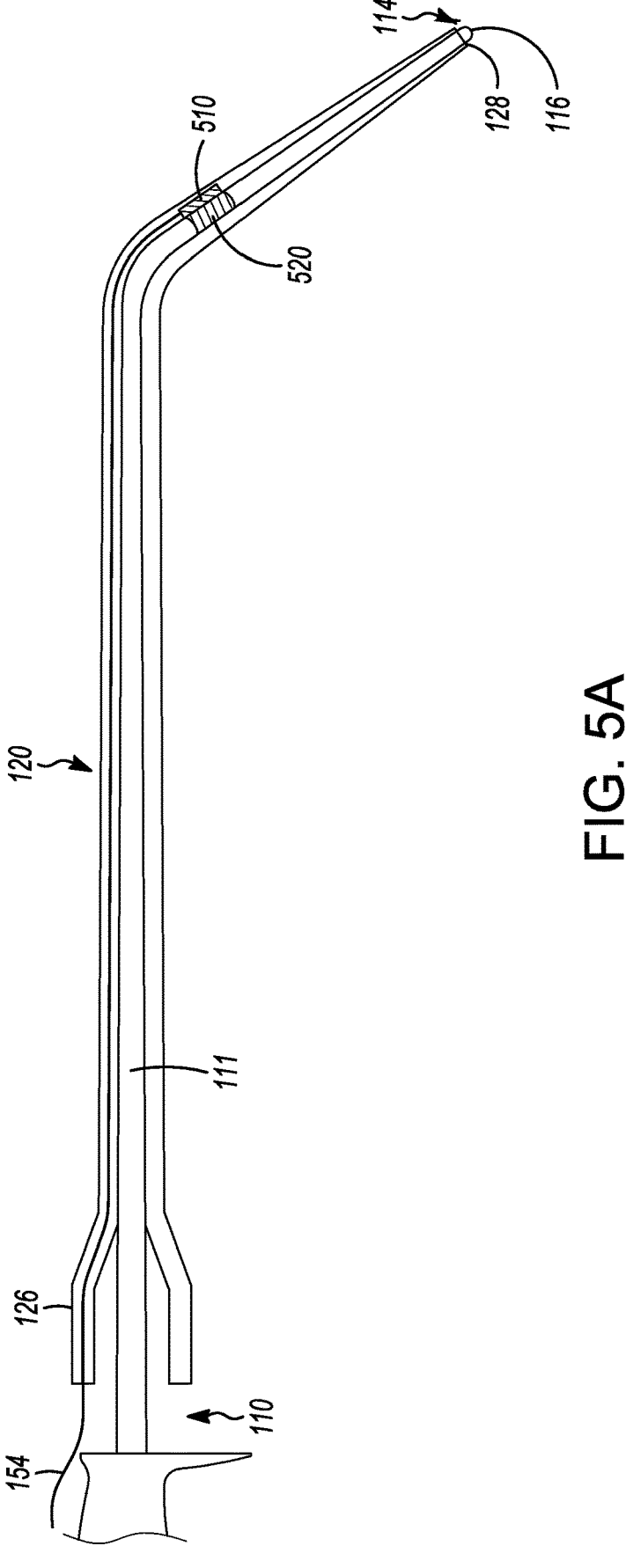
FIG. 5a-5c are illustrations of another embodiment wherein the dilator would deliver energy to the puncturing device via a conductive plate.
Figures 5B, 5C:
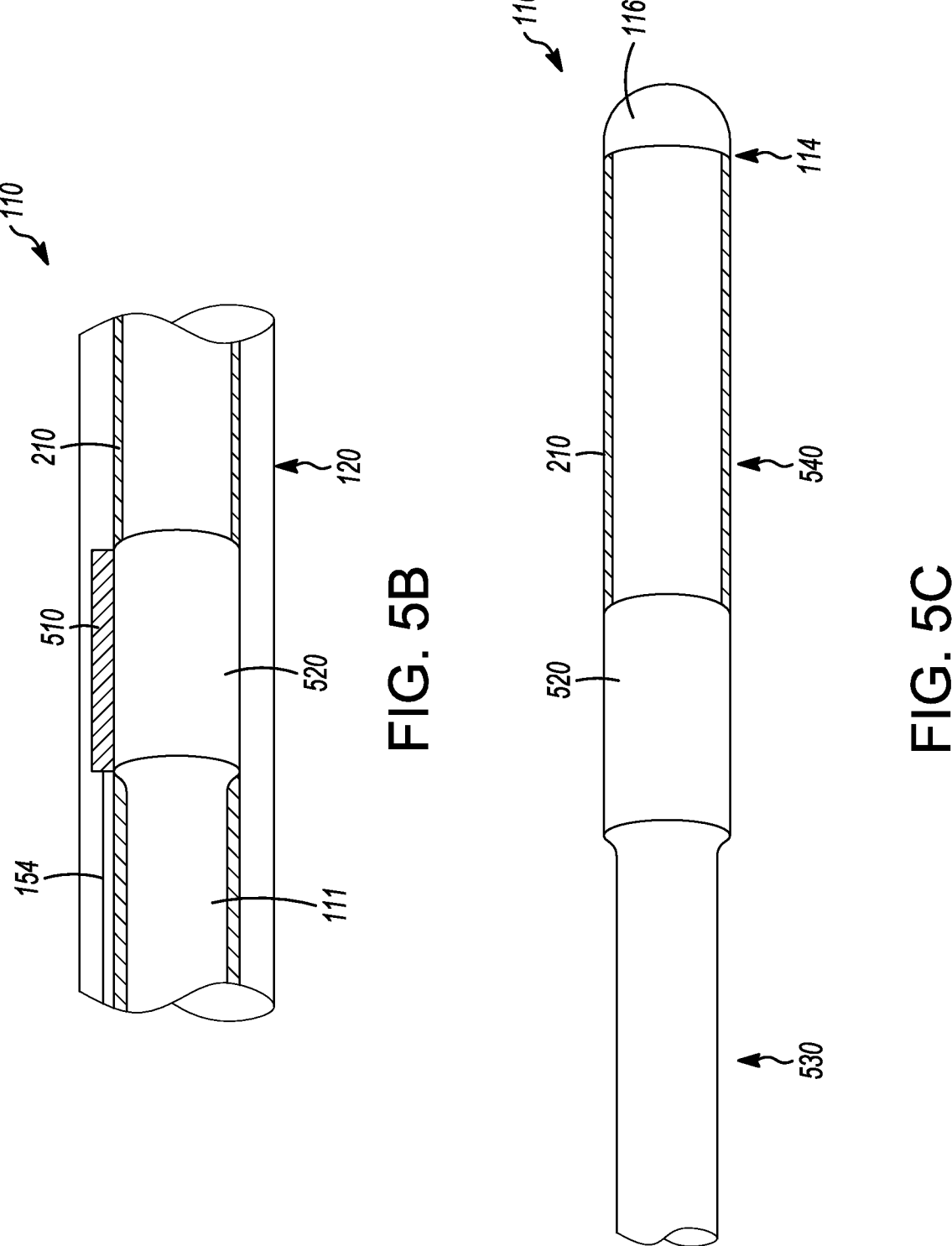

With reference now to FIG. 5*a*, in an alternative embodiment, the dilator 120 is the device that delivers energy from the generator to the energy delivery device 116 at the distal tip 114 of the puncturing device 110. The dilator 120 may be comprised of an electrically insulative material with a conductive plate 510 embedded into the sidewall of said dilator along the member 123, such that the plate 510 may contact the puncturing device 110. The dilator 120 may be comprised of a harder material, such as high-density polyethylene (HDPE) or a softer material, for example polyurethane or polyether block amide. The conductive plate 510 can deliver energy from the generator, via an insulated connecting cable 154, which exits the dilator hub 126 and connects to the generator. The puncturing device 110 comprises a conductive band 520 which may be composed of a non-conductive material doped with conductive material or a band comprised entirely of conductive material. The band 520 may be fitted via a mechanical fit that is swaged over the elongate member 111, or the band 520 may be fitted over the elongate member 111. The elongate member 111 of the puncturing device 110 may be comprised of a conductive material, such as a conductive hypotube or shaft, with an insulative coating 210 covering the entire elongate member 111, leaving the conductive band 520 exposed such that it is able to contact the conductive plate 510 of the dilator 120, as illustrated in FIG. 5*b*. The layer of insulation 210 may be one of many biocompatible dielectric materials, including, but not limited to, polytetrafluoroethylene (PTFE, Teflon®), parylene, polyimides, polyethylene, terephthalate (PET), polyether block amide (PEBAX®), and polyetheretherketone (PEEK™), or any combinations thereof. Alternatively, the elongate member may be manufactured such that it has a larger outer diameter in one section. This section would be exposed (i.e., not covered with insulative material) such that it is able to contact the conductive plate 510. In some embodiments, the elongate member 111 may be comprised of a non-conductive material proximal 530 to the conductive band 520, and a conductive material distal 540 of the conductive band 520 that has an insulative coating 210 over top (FIG. 5*c*). In an alternative embodiment, the conductive band 520 may be part of the distal 540 elongate member 111. For example, the outer diameter of the elongate member 111 may be larger such that it contacts the conductive plates 510. The conductive band 520 is in electrical communication with the energy delivery device 116 of the puncturing device 110. Energy delivery would only be enabled when the conductive plate 510 of the dilator 120 is in contact with the conductive band 520 of the puncturing device. When the energy delivery device 116 is slightly protruding from the distal tip 128 of the dilator 120, the conductive band 520 and plate 510 will be in contact with one another. This would allow the energy to flow from the generator to the conductive plate 510 of the dilator 120, and when in contact with the conductive band 520, to the energy delivery device 116 of the puncturing device 110. Upon completion of the puncture of tissue, the puncturing device 110 moves forward through the puncture and the contact between the conductive plate 510 and conductive band 520 is no longer present, disabling the delivery of energy.

US 12,588,947 B2

9
FURTHER EXAMPLES

1) An assembly to create a puncture in a tissue, comprising:
   A puncturing device comprising an elongate member having a distal tip configured to deliver energy to the tissue, creating the puncture;
   The puncturing device further comprises a marker positioned along the elongate member;
   A dilator wherein the dilator comprises a lumen extending from a proximal portion to a distal portion and configured to receive the puncturing device; and,
   The dilator further comprises a detector positioned along a length of the dilator;
   Whereby when the marker and the detector are aligned, energy is delivered to the distal tip of the puncturing device.
2) The assembly of example 1, wherein the marker is a colour band and the detector is a colour sensor.
3) The assembly of example 2, wherein the colour band comprises a spray coating.
4) The assembly of example 2, wherein the colour band comprises a sleeve of different colour positioned overtop the elongate member.
5) The assembly of any one of examples 3 or 4, wherein the elongate member comprises a coating of insulative material.
6) The assembly of example 5, wherein the coating of insulative material comprises a portion of clear coating positioned overtop the colour band.
7) The assembly of example 5, wherein the coating of insulative material comprises a clear coating extending the entire length of the elongate member.
8) The assembly of example 1, wherein the marker is a band with a barcode and the detector is a barcode reader.
9) The assembly of example 8, wherein the band comprises a sleeve positioned overtop the elongate member.
10) The assembly of example 9, wherein the sleeve comprises a unique barcode.
11) The assembly of example 9, wherein the sleeve is a solid color and an etching of lines is ablated onto the sleeve.
12) The assembly of any one of examples 9 to 11, wherein the elongate member comprises a coating of insulative material.
13) The assembly of example 12, wherein the coating of insulative material comprises a portion of clear coating positioned overtop of the band.
14) The assembly of example 12, wherein the coating of insulative material comprises a clear coating extending the entire length of the elongate member.
15) The assembly of example 1, wherein the marker is a band of a distinct surface roughness and the detector is a light intensity sensor.
16) The assembly of example 15, wherein the distinct surface roughness is applied directly to a surface of the elongate member.
17) The assembly of example 15, wherein the band is a separate piece, positioned overtop the elongate member.
18) The assembly of example 17, wherein the band is swaged over the elongate member.
19) The assembly of example 17, wherein the band is fit over top of the elongate member.
20) The assembly of any one of examples 16 to 19, wherein the elongate member comprises a coating of insulative material.
21) The assembly of example 20, wherein the coating of insulative material comprises a portion of clear coating positioned overtop of the band.
22) The assembly of example 20, wherein the coating of insulative material comprises a clear coating extending the entire length of the elongate member.
23) The assembly of example 1, wherein the marker is a magnetic band and the detector is a magnetic sensor.
24) The assembly of example 23, wherein the marker is positioned overtop the elongate member.
25) The assembly of example 23, wherein the marker is swaged over the elongate member.
26) The assembly of example 23, wherein the marker is comprised of a metal band.
27) The assembly of example 23, wherein the marker is comprised of a doped plastic band.
28) The assembly of any one of examples 24 to 27, wherein the elongate member comprises a coating of insulative material.
29) The assembly of example 27, wherein the doped plastic band comprises a heat shrinkable plastic tube doped with a magnetic material.
30) The assembly of a example 1, wherein the marker is a metal band and the detector is a capacitance proximity sensor.
31) The assembly of example 30, wherein the marker is positioned overtop of the elongate member.
32) The assembly of example 31, wherein the metal band is composed of a magnetic material.
33) The assembly of example 31, wherein the metal band is composed of a non-magnetic material.
34) The assembly of any one of examples 1 to 33, wherein the detector is embedded into a wall of the dilator.
35) An assembly to create a puncture in a tissue, comprising:
   A puncturing device comprising an elongate member having a distal tip configured to deliver energy to the tissue, creating the puncture;
   The puncturing device further comprises a detector positioned along the elongate member;
   A dilator wherein the dilator comprises a lumen extending from a proximal portion to a distal portion and configured to receive the puncturing device; and,
   The dilator further comprises a marker positioned along a length of the dilator;
   Whereby when the marker and the detector are aligned, energy is delivered to the distal tip of the puncturing device.
36) The assembly of example 35, wherein the marker is a colour band and the detector is a colour sensor.
37) The assembly of example 35, wherein the marker is a band with a barcode and the detector is a barcode reader.
38) The assembly of example 35, wherein the marker is a band of distinct surface roughness and the detector is a light intensity sensor.
39) The assembly of any one of examples 35 to 37, wherein the dilator comprises a portion of transparent material where the marker is located.
40) The assembly of example 35, wherein the marker is a magnetic band and the detector is a magnetic sensor.
41) The assembly of example 35, wherein the marker is a metallic band and the detector is a capacitance proximity sensor.

42) An assembly to create a puncture in a tissue, comprising:

A puncturing device comprising an elongate member having a distal tip configured to deliver energy to the tissue, creating the puncture;

The puncturing device further comprising a conductive band;

A dilator, wherein the dilator comprises a lumen extending from a proximal portion to a distal portion configured to receive the puncturing device; and, The dilator further comprises a conductive plate embedded into a side wall of the lumen;

Whereby when the conductive band of the puncturing device is proximate the conductive plate of the dilator, energy is delivered to the distal tip of the puncturing device.

43) The assembly of example 42, wherein the dilator is composed of an electrically insulative material.

44) The assembly of example 43, wherein the dilator is composed of one of or a combination of high-density polyethylene, polyurethane, or polyether block amide.

45) The assembly of example 42, wherein the dilator further comprises an insulative connection cable that runs from a proximal end of the dilator to the conductive plate.

46) The assembly of example 42, wherein the conductive band is comprised of a non-conductive material doped with a conductive material.

47) The assembly of example 42, wherein the conductive band is comprised entirely of a conductive material.

48) The assembly of any one of examples 46 or 47, wherein the conductive band may be swaged over the elongate member.

49) The assembly of any one of examples 46 or 47, wherein the conductive band is fitted over the elongate member.

50) The assembly of example 42, wherein the elongate member is comprised of a conductive material with an insulative coating extending over the entire length of the elongate member, and wherein the conductive band is positioned such that it is exposed from the insulative coating.

51) The assembly of example 50, wherein the conductive band is a portion of the elongate member that has an increased diameter such that it contacts the conductive plate of the dilator.

52) A method for creating a puncture in a septum of a heart using a puncture device with a marker positioned along a length of the puncture device and a dilator with a detector positioned along a length of the puncture device, wherein alignment of the marker and the detector would enable energy delivery, the method comprising the steps of:

Introducing an assembly of the puncture device and the dilator into a right atrium of the heart, wherein the puncturing device is received within the dilator such that the marker and the detector are not aligned;

Locating a target location on the septum with a distal tip of the assembly;

Aligning the marker and the detector to enable energy delivery to a distal tip of the puncture device; and, Advancing the puncture device such that the distal tip enters the left atrium, and whereby the marker and the detector are no longer align, disabling energy delivery.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. An assembly to create a puncture in a tissue, comprising:

a puncturing device comprising an elongate member having a distal tip configured to deliver energy to the tissue, creating the puncture;

the puncturing device further comprises a first element positioned along the elongate member;

a dilator wherein the dilator comprises a lumen extending from a proximal portion to a distal portion and configured to receive the puncturing device; and, the dilator further comprises a second element positioned along a length of the dilator;

wherein:

one of the first element and the second element is configured to send a signal to a generator when the first element and the second element are aligned, the signal being configured to enable energy delivery from the generator to the distal tip of the puncturing device; and absence of the signal disables energy delivery from the generator to the distal tip of the puncturing device.

2. The assembly of claim 1, wherein the first element is either a marker or a detector while correspondingly the second element is either the detector or the marker respectively.

3. The assembly of claim 2, wherein the elongate member comprises a coating of insulative material.

4. The assembly of claim 2, wherein the marker is a band with a barcode and the detector is a barcode reader.

5. The assembly of claim 2, wherein the marker is a band of a distinct surface roughness and the detector is a light intensity sensor.

6. The assembly of claim 2, wherein the marker is a magnetic band and the detector is a magnetic sensor.

7. The assembly of claim 2, wherein the marker is a metal band and the detector is a capacitance proximity sensor.

8. The assembly of claim 2, wherein the detector is embedded into a wall of the dilator.

9. The assembly of claim 2, wherein the marker is a colour band and the detector is a colour sensor.

* * * * *